United States Patent
Heller et al.

(10) Patent No.: US 6,385,080 B1
(45) Date of Patent: May 7, 2002

(54) DNA OPTICAL STORAGE DEVICE USING FÖRSTER ENERGY TRANSFER MECHANISM

(75) Inventors: Michael J. Heller, Encinitas; Eugene Tu, San Diego, both of CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/568,527

(22) Filed: May 9, 2000

Related U.S. Application Data

(63) Continuation of application No. 09/129,740, filed on Aug. 5, 1998, now Pat. No. 6,067,246, which is a continuation of application No. 08/906,569, filed on Aug. 5, 1997, now Pat. No. 5,835,404, which is a continuation of application No. 08/258,168, filed on Jun. 10, 1994, now Pat. No. 5,787,032, which is a continuation-in-part of application No. 08/232,233, filed on May 5, 1994, now Pat. No. 5,565,322, which is a continuation-in-part of application No. 07/790,262, filed on Nov. 7, 1991, now abandoned.

(51) Int. Cl.[7] .............................. G11C 13/00; G11B 7/00
(52) U.S. Cl. ...................... 365/151; 365/112; 365/106; 365/234; 369/108; 369/100; 369/284; 369/288
(58) Field of Search ................................. 365/106, 107, 365/112, 119, 151, 234; 369/100, 108, 284, 288; 430/270.19, 495.1, 496; 435/6

(56) References Cited

U.S. PATENT DOCUMENTS

| | | | |
|---|---|---|---|
| 4,032,901 A | 6/1977 | Levinthal | 365/118 |
| 4,728,724 A | 3/1988 | Jones, Jr. et al. | 430/19 |
| 4,996,143 A | 2/1991 | Heller et al. | 435/6 |
| 5,231,626 A | 7/1993 | Tadokoro et al. | 369/121 |
| 5,316,900 A | 5/1994 | Tsujioka et al. | 430/270.15 |
| 5,346,789 A | 9/1994 | Lewis et al. | 430/19 |
| 5,373,491 A | 12/1994 | Terao et al. | 369/102 |
| 5,399,451 A | 3/1995 | Hashida et al. | 430/19 |
| 6,107,038 A * | 8/2000 | Choudhary et al. | 435/6 |

FOREIGN PATENT DOCUMENTS

| | | | | |
|---|---|---|---|---|
| DE | 42 18 036 A | 12/1992 | | G11B/7/24 |
| EP | 0 354 601 A | 2/1990 | | G11B/7/24 |
| EP | 0 503 428 A | 9/1992 | | G11B/7/24 |
| WO | WO 93 09128 A | 5/1993 | | C07H/21/04 |
| WO | WO 93 11470 A | 6/1993 | | G03G/7/00 |

OTHER PUBLICATIONS

Proc. Natl. Acad. Sci. USA, vol. 82, Apr. 1985, Haddon et al, "The Molecular Electronic Device and the Biochip Computer: Present Status", pp 1874–1878.

(List continued on next page.)

*Primary Examiner*—Andrew Q. Tran

(57) ABSTRACT

An optical memory system includes memory cells which utilize synthetic DNA as a component of the information storage mechanism. In the preferred embodiment, memory cells contain one or more chromophoric memory units attached to a support substrate. Each chromophoric memory unit comprises a donor, an acceptor and, at some time during its existence, an active quencher associated with the donor and/or the acceptor. The donor and the acceptor permit non-radiative energy transfer, preferably by Förster energy transfer. To write to the memory cell, the quencher is rendered inactive, preferably by illumination with ultraviolet light. To read, the chromophoric memory units in a read portal are illuminated, and the read illumination is detected. In the preferred embodiment, multiple chromophoric memory units having resolvable read properties are contained within a single read portal. In this way, a multibit word of data may be read from a single diffraction limited read portal. In one aspect of this invention, the read portal is subdivided into multiple write sub-locations, where each sub-location contains chromophoric memory units with acceptors which emit at spectrally resolvable colors. In a further aspect, each sub-location provides variable output based on wavelength, intensity and/or polarization.

20 Claims, 11 Drawing Sheets

OTHER PUBLICATIONS

Proc. Natl. Acad. Sci. USA, vol. 83, Dec. 1988, Cardullo et al., "Detection of Nucleic Acid Hybridization by Nonradiative Fluorescence Resonance Energy Transfer", pp 8790–8794.

Vivian Moses, "Bioelectronics: 'Biochips'", Biotechnology The Science and the Business, Ch. 21, pp 371–378.

Robinson, et al., "The Design of a Biochip: A Self-Assembling Molecular Scale Memory Device", *Protein Engineering*, 1:295–300 (1987).

Halfhill, Tom, R., "New Memory Architectures to Boost Performance", Byte, Jul., 1993, pp 86–87.

* cited by examiner

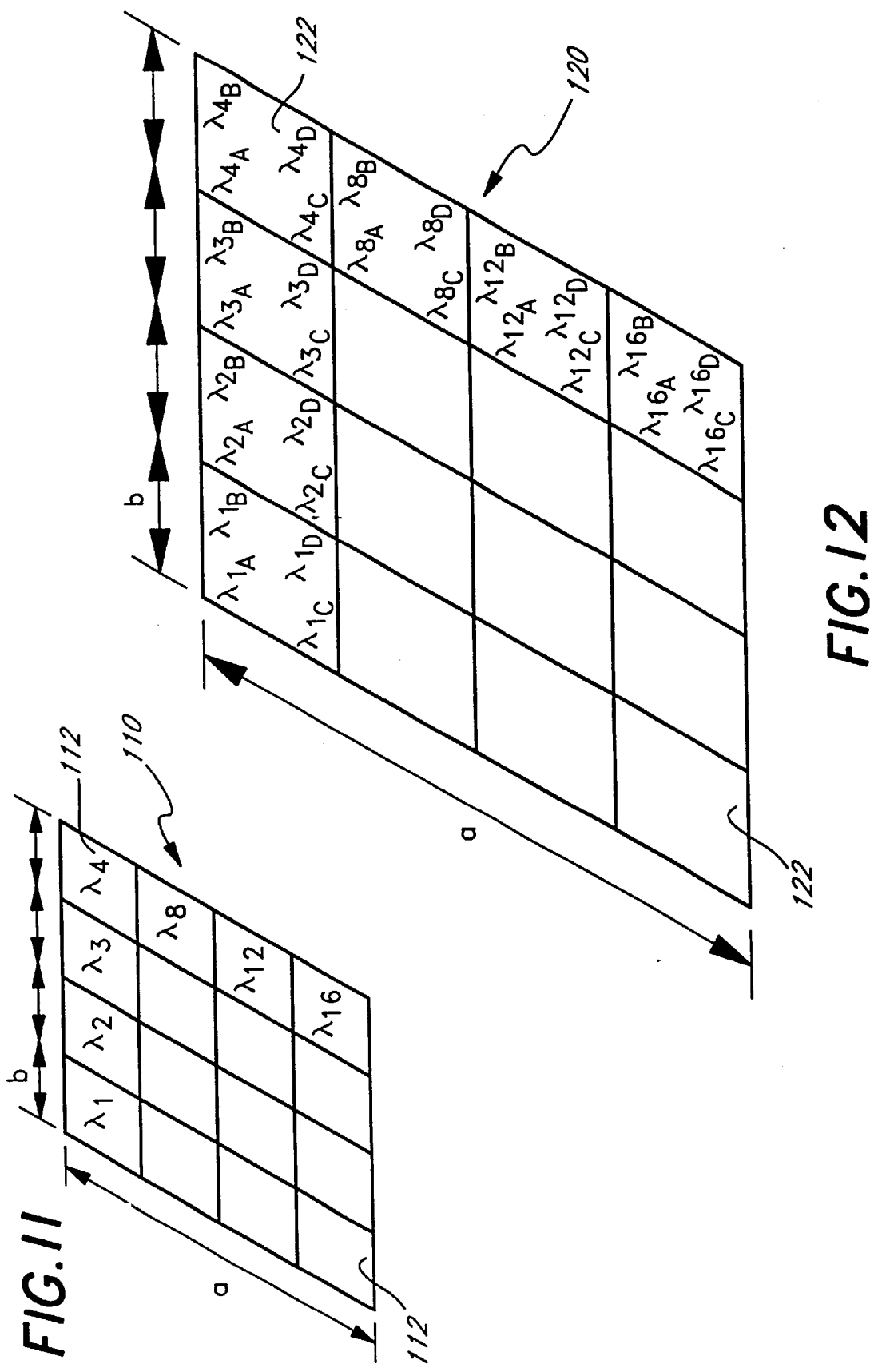

DNA POLYMER SEQUENCE

```
AT7                                                        ********** ********** ***A
AT5                                              ********** ********TA
     5' GACTTGACCT GAGGACCCGA TCGGCTAGCC CCTGCTCATG AGTCTCTCGT GCGAGCTGCA GTCAGACATA GTC 3'
     3' CTGAACTGGA CTCCTGGGCT AGCCGATCGG GGACGAGTAC TCAGAGAGCA CGCTCGACGT CAGTCTGTAT CAG 5'
AT1 ATAA**********
AT2 ATAA**********
AT4      ATG**********
AT6                A*                                ********** **********
AT8                A*                                ********** ********** TT
ET10AL                                                        **********
ET14C         ********** ********** ***N
ET16          ********** ********** ***N
ET20                                                                   **********N

AT3 5' CGCACTATGG TCGTGAGTGT TCAGAGGCTA A  3'                      A **********

REPETITIVE OR DEGENERATE SEQUENCE MODEL SYSTEM:

T2       N********* **********
      5' TTTTTTTTT TTTTTTTTT  3'
      3' AAAAAAAAA AAAAAAAAA  5'
CP1      U********* **********
POLY rA A********* **********...n  WHERE n = 300-500 BASES

KEY: N = 5  AMINE
     t =    INTERNAL AMINE
     F =    FLUORESCEIN
     A,U = 3  RIBONUCLEOSIDE
```

DNA OPTICAL STORAGE DEVICE USING FORSTER ENERGY TRANSFER MECHANISM

This is a continuation of application Ser. No. 09/129,740, filed Aug. 5, 1998, now U.S. Pat. No. 6,067,246, which is a continuation of application Ser. No. 08/906,569 filed Aug. 5, 1997, now U.S. Pat. No. 5,835,404, which is continuation of application Ser. No. 08/258,168, filed on Jun. 10, 1994, now U.S. Pat. No. 5,787,032, which is a continuation-in-part of Ser. No. 08/232,233, filed May 5, 1994, now U.S. Pat. No. 5,565,322, which is a continuation-in-part of Ser. No. 07/790,262, filed Nov. 7, 1991, now abandoned, which was continued into Ser. No. 08/250,951, filed May 27, 1994, now U.S. Pat. No. 5,532,129.

FIELD OF THE INVENTION

This invention relates to information storage devices. More particularly, it relates to the use of synthetic DNA polymers for information storage in memory, most particularly secondary optical storage mass memory.

BACKGROUND OF THE INVENTION

Historically, data processing engines have been physically and conceptually separated from the memory which stores the data and program commands. As processor speed has increased over time, there has been a continuous press for larger memories and faster access. Recent advances in processor speed have caused system bottlenecks in access to memory. This restriction is critical because delays in obtaining instructions or data may cause significant processor wait time, resulting in loss of valuable processing time.

Various approaches have been taken to solve these concerns. Generally, the solutions include using various types of memory which have different attributes. For example, it is common to use a relatively small amount of fast, and typically expensive, memory directly associated with the processor units, typically called cache memory. Additionally, larger capacity, but generally slower, memory such as DRAM or SRAM is associated with the CPU. This intermediate memory is often large enough for a small number of current applications, but not large enough to hold all system programs and data. Mass storage memory, which is ordinary very large, but relatively inexpensive, is relatively slow. While advances have been continually made in improving the size and speed of all types of memory, and generally reducing the cost per bit of memory, there remains a substantial need especially to serve yet faster processors.

For the last 20 years most mass storage devices have utilized a rotating memory medium. Magnetic media have been used for both "floppy" (flexible) disks or "hard" disk drives. Information is stored by the presence or absence of magnetization at defined physical locations on the disk. Ordinarily, magnetic media are "read-write" memories in that the memory may be both written to and read from by the system. Data is written to or read from the disk by heads placed close to the surface of the disk.

A more recent development in rotating mass storage media are the optical media. Compact disks are read only memory in which the presence or absence of physical deformations in the disk indicates the data. The information is read by use of a focused laser beam, in which the change in reflectance properties from the disk indicate the data states. Also in the optical realm are various optical memories which utilize magneto optic properties in the writing and reading of data. These disks are both read only, write once read many ("WORM") drives and multiple read-write memories. Generally, optical media have proved to have a larger storage capacity, but higher costs per bit and limited write ability, as compared with magnetic media.

Several proposals have been made for using polymers for electronic based molecular memories. For example, Hopfield, J. J., Onuchic, J. N. and Beratan, D. N., "A Molecular Shift Register", Science, 241, p. 817, 1988, discloses a polymer based shift register memory which incorporates charge transfer groups. Other workers have proposed an electronic based DNA memory (see Robinson et al, "The Design of a Biochip: A Self-Assembling Molecular-Scale Memory Device", *Protein Engineering*, 1:295–300 (1987)). In this case, DNA is used with electron conducting polymers for a molecular memory device. Both concepts for these molecular electronic memories do not provide a viable mechanism for inputting data (write) and for outputting data (read).

Molecular electronic memories have been particularly disappointing in their practical results. While proposals have been made, and minimal existence proofs performed, generally these systems have not been converted to commercial reality. Further, a specific deficiency of the system described above is that a sequential memory is typically substantially slower than a random access memory for use in most systems.

The optical memories described above suffer from the particular problem of requiring use of optical systems which are diffraction limited. This imposes size restrictions upon the minimum size of a data bit, thereby limiting memory density. This is an inherent limit in systems which store a single bit of data at a given physical memory location.

Further, in all optical memory systems described above, the information is stored on a bit-by-bit basis, such that only a single bit of data is obtained by accessing a giving physical location in memory. While word-wide memory access systems do exist, generally they store but a single bit of information at a given location, thereby requiring substantially the same amount of physical memory space whether accessed in a bit manner or word-wide manner.

While systems have generally increased in speed and storage density, and decreased in cost per bit, there remains a clear gap at present between processor speed and system requirements. See generally, "New Memory Architectures to Boost Performance", Tom R. Halfhill, Byte, July, 1993, pp 86 and 87. Despite the general desirability of memories which are faster, denser and cheaper per bit, and the specific critical need for mass memory which can meet the demands of modern day processor systems speed, no completely satisfactory solution has been advanced heretofore. The fundamental limitations on the currently existing paradigms cannot be overcome by evolutionary enhancements in those systems. This invention constitutes a new memory paradigm.

SUMMARY OF THE INVENTION

Synthetic DNA polymers are used as an optical storage media for memory. In the preferred embodiment, a three-dimensional memory is formed having three spatial dimensions. Multiple bit information is read as different color wavelengths of light emitted through diffraction limited optical portals on the surface of the media.

Structurally, a planar substrate (x-y dimension) has multiple, physically separate read portals or read locations disposed upon its surface. In the preferred embodiment, the substrate is disk shaped and the read portals are arranged in radial tracks or on a decreasing radius spiral around the center of the substrate. The read portal is that area which will be illuminated by a read illumination source to provide output from the memory. The read portal contains within it one or more DNA chromophoric memory units. In the preferred embodiment, each DNA chromophoric memory unit is composed of a DNA template, onto which are attached donor and acceptor units. Functionalized DNA polymers have various arrangements of chromophoric donors, chromophoric acceptors and quenchers. The quenchers are associated with the donor and/or the acceptor. The functionalized DNA polymers containing the donor/acceptor/quencher groups are arranged on the planar surface of the media so as to project into the z-spatial dimension. The chromophoric memory unit is attached to the substrate.

To write to the memory, the response properties of the chromophoric memory unit are changed. In the preferred embodiment, a photochemical reaction destroys or inactivates the quencher. A write source serves as the illumination source for the photochemical reaction. In the preferred embodiment, the quencher may be inactivated by light, most preferably UV light, and is formed with photocleavable linkers, or by derivitization of chromophore molecules with photoactive groups. Thus, the basic memory information is determined by whether the quencher is active or not.

To read from the memory, preferably a single wavelength light is used to illuminate the read portal. A read illumination source illuminates the read portal, including the various chromophoric memory units contained within the portal, providing excitation illumination to the donor units in the chromophoric memory units. If the quencher is not active, the chromophoric memory unit, via the acceptor, radiates to the read detector. However, if the qencher is active, no output occurs. In this way, all chromophoric memory units in a read portal may be simultaneously probed. If multiple chromophoric memory units having various output wavelengths or other detectable parameters are included within a read portal, a multiple bit or word-wide output may be obtained from a diffraction limited read portal.

In the preferred embodiment, the chromophoric memory unit utilizes energy transfer between the donor and acceptor, via the Förster energy transfer mechanism. Förster energy transfer is a non-radiative energy transfer mechanism which utilizes dipole-dipole coupling. The energy transfer mechanism allows a single wavelength of light to excite all acceptor chromophores.

In one embodiment, multiple write wavelengths are used to selectively activate or deactivate separate wavelength sensitive quenchers. If multiple wavelength sensitive quenchers are utilized, the various chromophoric memory units located within a given read portal may have various chromophoric responses. Multiple write wavelengths may then be selectively used to activate or inactivate quenchers. Upon illumination from the read illumination source, those chromophoric memory units whose output is not quenched will provide multiple wavelength output to the read detector. However, those chromophoric memory units whose output is quenched will not provide output.

In another embodiment, the read or optical portal is further spatially subdivided (x-y dimension) into multiple write sublocations. Each write sublocation is written to separately from the other write sublocations in a read portal. In the preferred embodiment, a given write sublocation contains chromophoric memory units whose primary output wavelength is spectrally resolvable as compared to the output from other write sublocations. By writing separately to the individual write sublocations, a single quencher material may be used for multiple read wavelengths.

In another aspect of this invention, the output of the read wavelength from the write sublocation may be varied. In the preferred embodiment, small wavelength shift substrates, various intensity states and/or polarization states may be affected by the use of multiple quenchers activated by different write wavelengths. By way of example, utilizing a read portal of approximately 1 micron$^2$, 16 separate write sublocations may be formed. Utilizing separate chromophoric acceptors for each of the write sublocations results in a 16 bit wide word output from the read portal. Utilizing one of the variations of wavelength shift substrates, intensity states and/or polarization states can directly produce a 64 bit wide word from a single sub-micron sized or diffraction limited read portal.

Accordingly, it is an object of this invention to provide an improved mass storage system.

It is yet a further object of this invention to provide a mass storage system with word-wide data output from a single potentially diffraction limited read location.

It is yet a further object of this invention to increase the planar surface storage density and capacity of memory.

It is an object of this invention to provide a memory having an increased data transfer rate.

It is yet a further object of this invention to provide a nanoscale storage location for memory applications.

It is a object of this invention to utilize functionalized synthetic DNA polymers for non-biological applications.

It is yet a further object of this invention to provide a write once read many (WORM) disk drive.

It is yet a further object of this invention to utilize synthetic DNA polymers as a memory material.

It is yet a further object of this invention to utilize synthetic DNA polymers as a nanofabrication material.

BRIEF DESCRIPTION OF THE DRAWINGS

FIG. 11 shows multiple write sublocations within a read portal.

FIG. 12 shows various write sublocations having secondary variations.

FIGS. 17a and 17b show an enhanced DNA polymer map.

DETAILED DESCRIPTION OF THE DRAWINGS

Figure 1A:
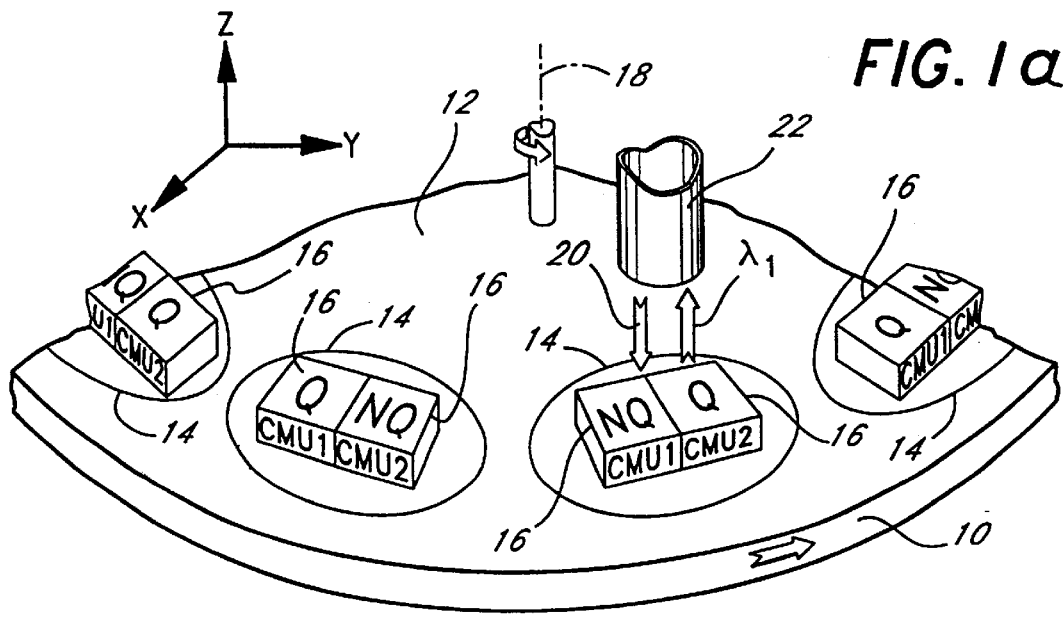
FIGS. 1a and 1b show a perspective view of a DNA optical storage system.

FIG. 1 shows a perspective view of a portion of the optical memory in accordance with this invention. A substrate 10 includes at least a first planar face 12 on which multiple read portals 14 may be located. An arbitrary x-y-z coordinate system is shown, where the x-y plane is parallel to the planar face 12 of the substrate 10, and the z-axis is perpendicular to the planar face 12. The substrate is preferably in the form of a round platter or platten. In the preferred embodiment, the substrate 10 is adapted to be rotated about a central axis of rotation 18. The read portals 14 are those physically defined locations in which various chromophoric memory units 16 are located. The read portal 14 may be formed in any geometric shape desired, such as a circle, oval, square or rectangle. Generally, the shape of the read portal 14 is based upon ease of manufacture and the ability to write to and read from a given read portal 14. As desired, the read portal 14 may be formed directly on the substrate 12, or alternatively, may be formed in a well or lowered region beneath the planar surface 12 or on a locally raised surface. In the preferred embodiment, each read portal 14 would be on the order of 1 micron wide.

The read portals 14 contain multiple chromophoric memory units 16. Each chromophoric memory unit contains at least a donor, an acceptor, and, at some time during its existence, an associated quencher. The linear synthetic DNA polymers which compose the chromophoric memory unit are preferably arranged in the z-dimension, relative to the planar (x-y) surface.

The chromophoric memory unit 16 is taken to be the basic memory element of the system. A given read portal 14 may contain multiple identical chromophoric memory units 16, the structure of FIG. 1 showing a single chromophoric memory unit for simplicity. The chromophoric memory unit 16 operates as a memory, that is, to indicate the state of information, based upon the presence or absence of effective quenching. When a quencher is active in conjunction with a donor and/or acceptor of a given chromophoric memory unit 16, such unit would not emit radiation from the acceptor under illumination of the donor. If no effective quenching occurs, the acceptor will reradiate energy received by the donor and transferred to it through a non-radiative transfer process. Thus, the absence of a quencher may be considered to be a "1" and the presence of a quencher considered to be a data bit "0". Of course, the convention of "1" and "0" may be reversed. While a digital scenario is presented, the chromophoric memory units could also be designed to emit in an "analog" fashion, such as intensity or flux levels.

Figure 1B:
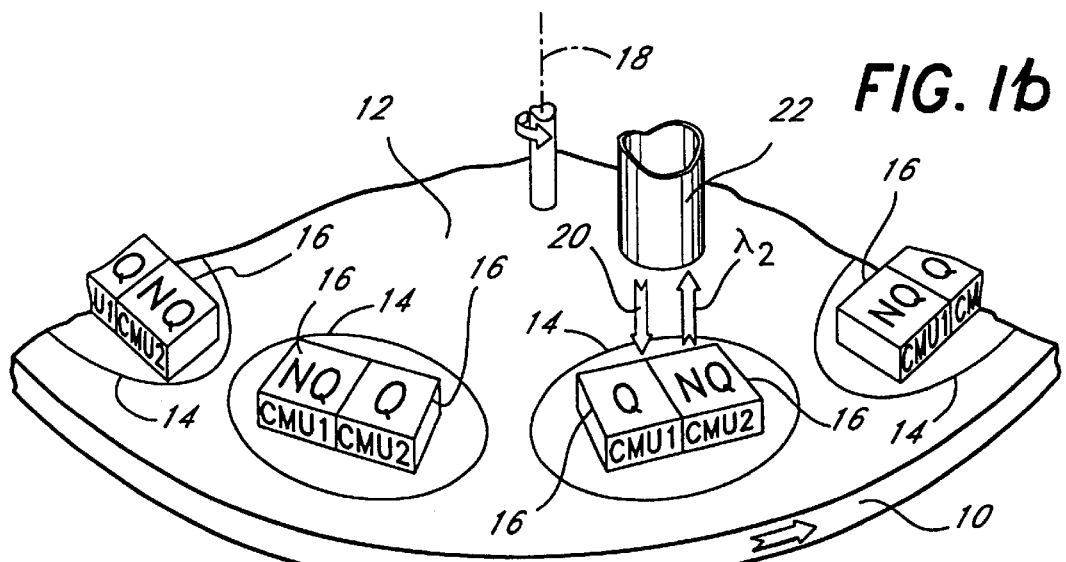

The operation of the memory system in a simple embodiment is shown in FIGS. 1a and 1b. This illustrates a memory in which each read portal 14 contains two distinct chromophoric memory units 16. These two units are distinct in that they have a detectable difference in their output, such as spectrally resolvable wavelengths, intensity differences or polarization states. In the preferred embodiment, each chromophoric memory unit will provide a spectrally resolvable different wavelength as an output. Further, each chromophoric memory unit 16 is either quenched (designated "Q") or not quenched (designated "NQ"). This quenching state is set during the write operation, which is illustrated in connection with FIGS. 5, 7, 8 and 15.

In the read operation, as the substrate 10 rotates around its axis of revolution 18, a first read portal 14 would be illuminated by light 20 from a read illumination source. The read illumination or beam can be applied through the detector device via a dichroic mirror or from an illumination source below the planar surface of the media. In both cases, the read beam impinges the media from the z-direction. In the drawing of FIG. 1a, the right hand complete optical portal 14 is illuminated by light 20, and provides output at $\lambda_1$ to a detector 22. Since chromophoric memory unit 16 (labelled CMU1) is not quenched, the read illumination 20 causes emission to the detector 22 at wavelength $\lambda_1$. However, since the chromophoric memory unit 16 (labelled CMU2) is quenched, the read illumination 20 does not result in output at $\lambda_2$. FIG. 1b shows the system of FIG. 1a when the substrate 10 has rotated such that the next read portal 14 is illuminated by the read illumination 20. Since chromophoric memory unit 16 labelled CMU1 is quenched, no output occurs at $\lambda_1$. However, since chromophoric memory unit 16 (labelled CMU2) is not quenched, read illumination 20 causes output at wavelength $\lambda_2$ to detector 22.

Expanding the examples of FIGS. 1a and 1b, if the chromophoric memory units 16 had units CMU1 and CMU2 which were quenched, there would be no output at either $\lambda_1$ or $\lambda_2$. Conversely, if both chromophoric memory units 16 labelled CMU1 and CMU2 were not quenched, there would be output from the optical portal 14 upon read illumination 20 at both wavelength $\lambda_1$ and $\lambda_2$.

In its simplest embodiment, each read portal 14 could contain but a single type of chromophoric memory unit. Information would be stored based upon the quenching or absence of quenching in the chromophoric memory unit 16. Each read portal 14 would hold a single bit of information. In the more preferred embodiment, the read portal 14 contains multiple chromophoric memory units 16 which provide resolvable output information. In this way, read illumination 20 on a single read portal 14 can produce a multibit word read. An effective 3-dimensional physical memory is thus formed, two dimensions being formed by the planar (x-y) dimensions of the read portal 14 and one dimension (z) being formed by arrangement of the chromophores in the DNA polymers, where information is output as multiple wavelengths. Parallel data access results in an effectively 4-dimensional memory.

One advantage of such structure is the increase in density of the memory. If the dimension of the optical read illumination 20 is constrained to be a certain size, such as a minimum size imposed by diffraction limits, the ability to provide resolvable data in the wavelength variable greatly increases the physical storage capacity of the memory. The type of memory described in connection with FIG. 1 is generally of the type which is write once, read many or "WORM" drives.

Figure 2:
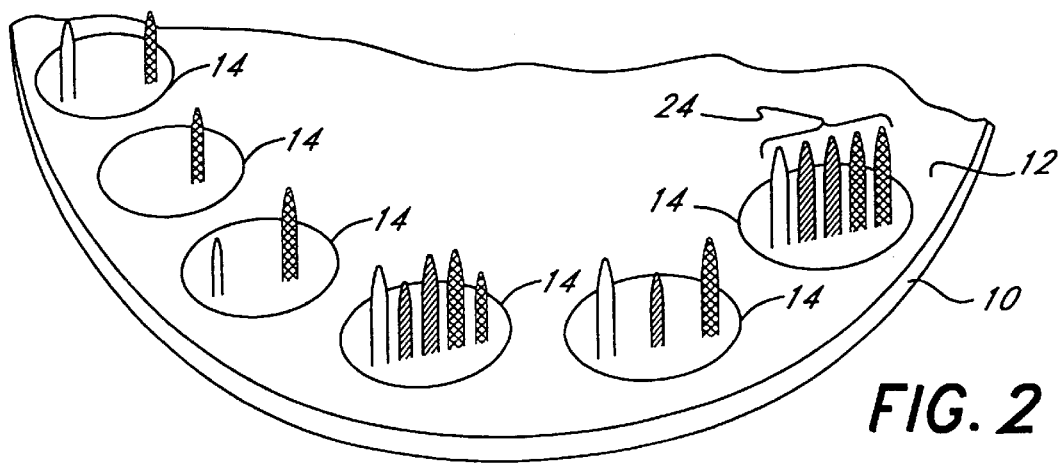
FIG. 2 shows a perspective, stylized view of the optical memory.

FIG. 2 shows a perspective, stylized view of the optical memory. The substrate 10 has multiple optical portals 14 disposed upon its surface 12. The optical memory would include many other such optical portals 14, but the number is reduced here for simplicity. The condition of the portals 14 in FIG. 2 is schematic in that each portal 14 is shown outputting read illumination. This ordinarily would occur only from a single optical portal 14 at a given time under action of the read illumination. The right most read portal 14 shows five separate output radiations 24. The remaining optical portal 14 viewed from right to left respectively show output of 3, 5, 2, 1 and 2 wavelengths 24. The output wavelengths 24 are intended to indicate output from chromophoric memory units which do not have their outputs quenched at these various output wavelengths 24. Additionally, FIG. 2 shows output wavelength 24 at varying heights intended to indicate intensity. The intensity of the output wavelength 24 is correlated with the amount of chromophoric memory units at a given wavelength which are not quenched.

Figure 3:
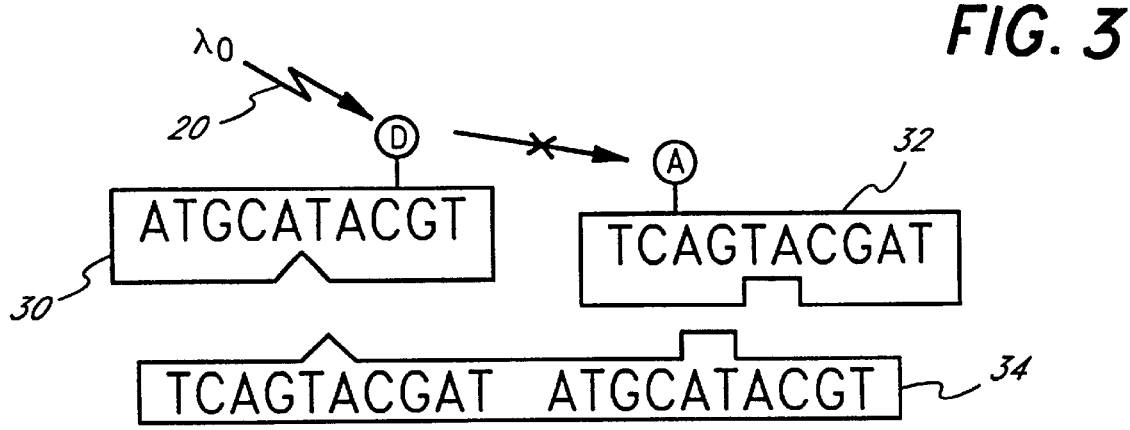
FIG. 3 shows a schematic version of a nonhybridized donor and acceptor adjacent a DNA backbone.

FIG. 3 shows a schematic view of self-organized building blocks. Here, a chromophore donor 30 and acceptor 32 have not hybridized with the template sequence 34. Thus, even when subject to read illumination 20, no energy transfer occurs between the donor 30 and acceptor 32. The base sequences shown are illustrative only of the concept, and are not actual intended sequences.

Figure 4:
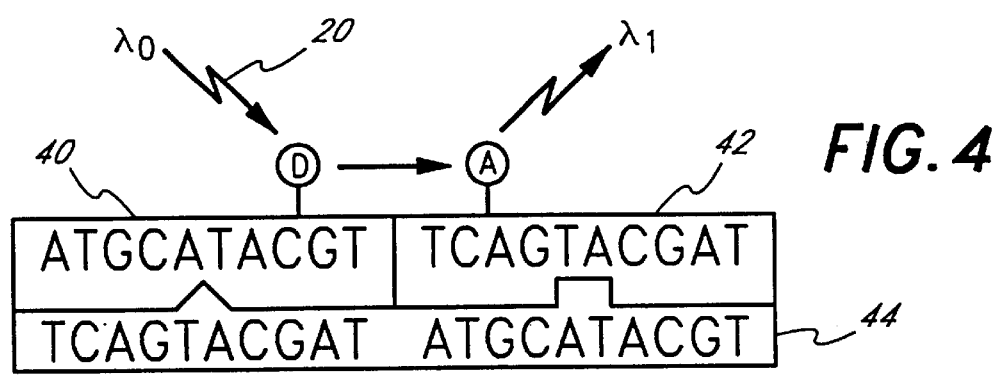
FIG. 4 shows a schematic version of hybridized DNA with basic Förster energy transfer.

FIG. 4 shows a hybridized structure in which the donor 40 and acceptor 42 are hybridized with the template 44. In this arrangement, energy transfer can occur between the donor 40 and acceptor 42. When read illumination 20 irradiates the donor 40, energy transfer may occur to the acceptor 42 which results in radiation of energy shown as $\lambda_1$. Energy transfer refers to the photonic process in which energy from the donor molecule 40 is transferred to the acceptor molecule 42 nonradiatively via dipole-dipole coupling. The acceptor 42 reemits light at a longer wavelength than the read illumination wavelength 20. Such dipole-dipole energy transfer is referred to as Förster energy transfer. This process is highly dependent on the distance between molecular centers, the phenomenon having a $1/r^6$ distance dependency where r equals half the distance between molecular centers.

Figure 5:
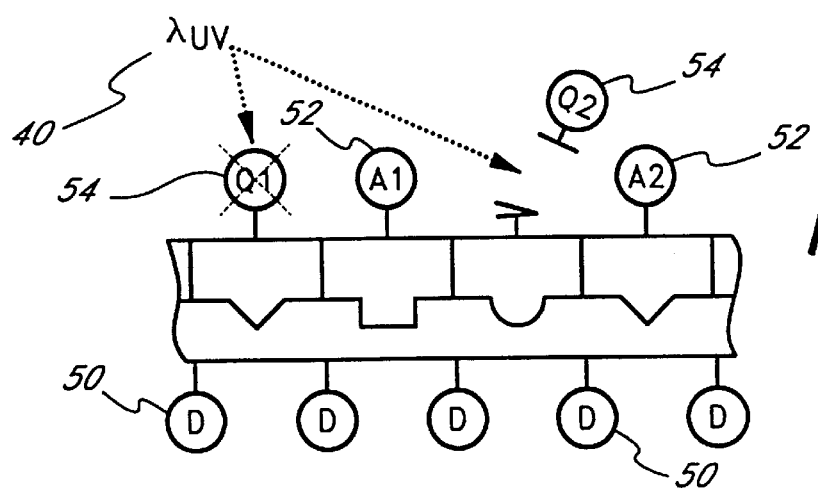
FIG. 5 shows the basic photo-write operation.
Figure 6:
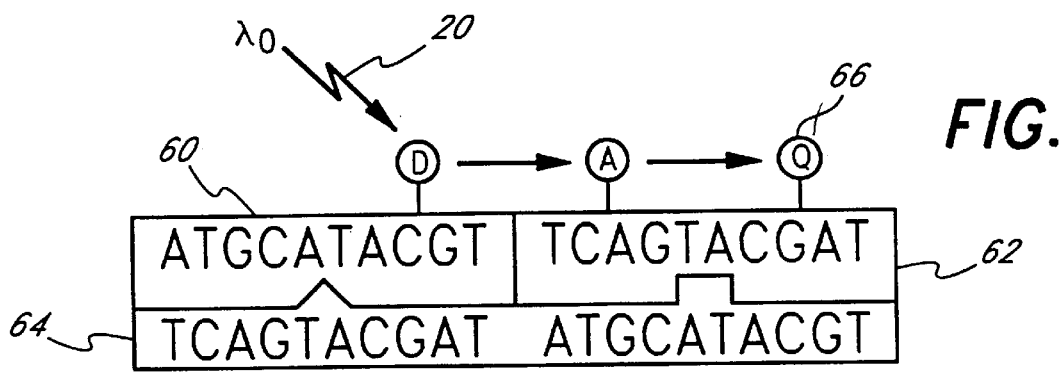
FIG. 6 shows the hybridized DNA with energy transfer quenched.

FIG. 5 shows a schematic version of the basic photo-write process. A series of donors 50 are associated with acceptors 52 such as acceptor $A_1$ and $A_2$. The acceptors 52 and donors 50 may be hybridized with a template (not shown). Quenchers 54 are disposed in effective proximity to acceptors 32. The quencher 54 labelled Q, is shown to be inhibited by the action of the write wavelength 40, as indicated by the "x". The quencher 54 labelled Q2 is shown subject to a destructive photo-write action from the write wavelength 40 as indicated by its disassociation from its attachment. FIG. 6 shows a donor 60 and acceptor 62 hybridized with a DNA backbone or template 64. A quencher 66 is still shown as present. Accordingly, the excitation radiation 20 $\lambda_0$ will be received by the donor 60, and passed to the acceptor 62, but energy will not be radiated by the acceptor 62 because of the presence of the quencher 66.

Figure 7A:
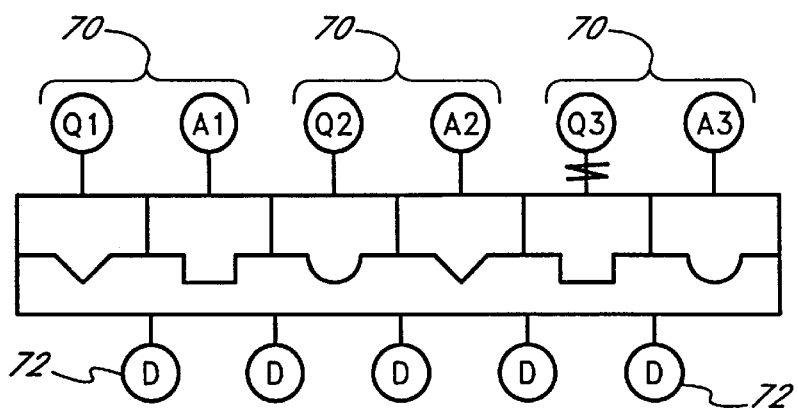
FIG. 7a, 7b, and 7c show a schematic overview of the operation, in FIG. 7a showing an off state, in FIG. 7b the photowrite process, and in FIG. 7c the read step.
Figure 7B:
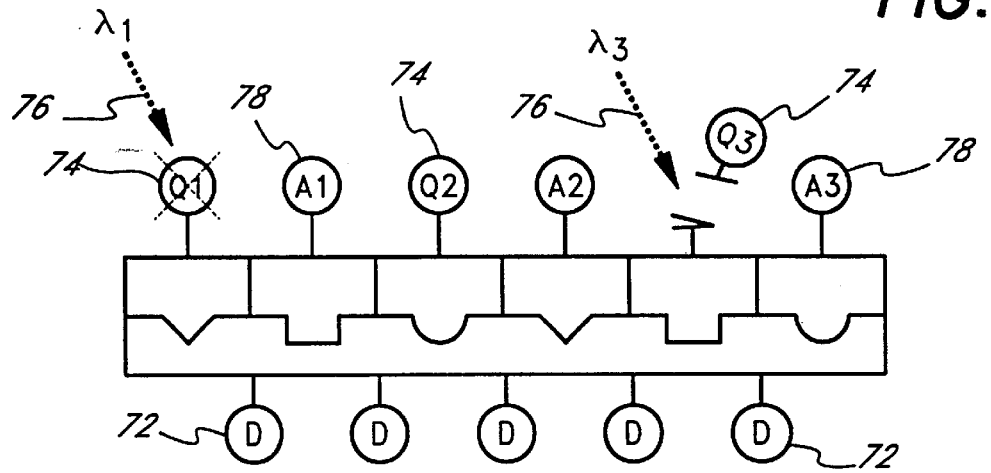
Figure 7C:
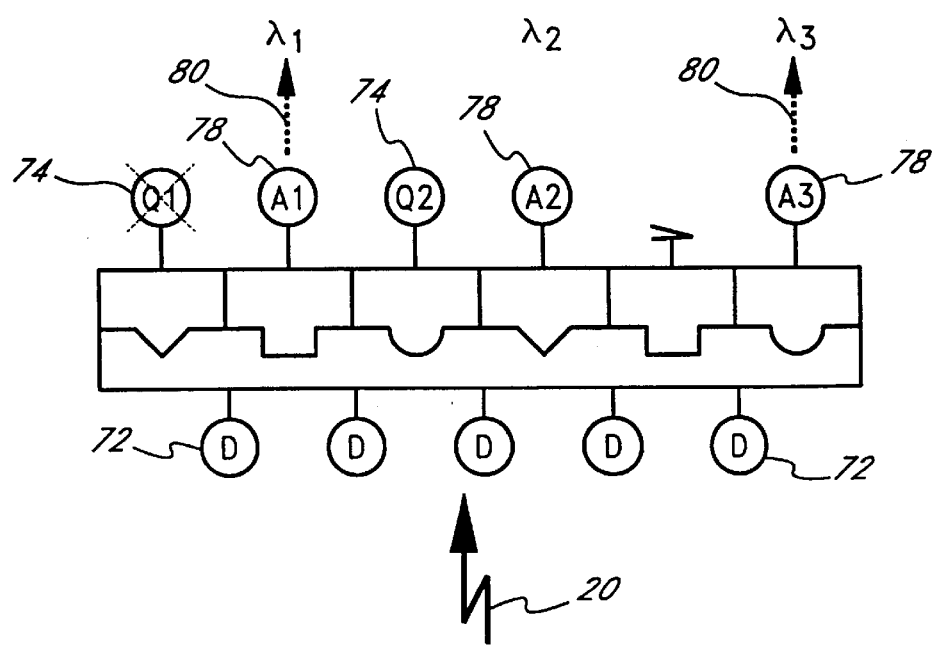

FIG. 7 shows a schematic version of the overall operation of the memory. In FIG. 7a, multiple chromophoric memory units are shown in the "off" stage, prior to any writing to the memory. Pairs of quenchers and acceptors 70 are located in effective energy transfer relationship with the donors 72. As shown in FIG. 7b, during the photo-write operation, the write wavelength effective for various quencher groups acts upon the quenchers responsive thereto. For example, the quencher 74 labelled Q1 is inhibited by the write wavelength 76 labeled $\lambda_1$. The quencher 74 labeled Q3 is destructively written to by write energy 76 at wavelength $\lambda_3$. As shown in FIG. 7(c), during the read operation, read illumination 20 at wavelengths $\lambda_1$ provides energy to the donors 72. Since acceptors 78 labeled A1 and A3 are not subject to the influence of quenchers 74 labeled Q1 and Q3, radiative emission of read energy 80 may occur at both $\lambda_1$ and $\lambda_3$. Conversely, since quencher 74 labeled Q2 inhibits acceptor 78 labeled A2, no read energy occurs at wavelength $\lambda_2$.

Figure 8A:
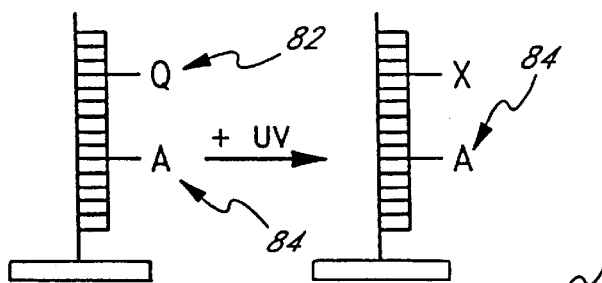
FIGS. 8a, 8b, and 8c show the write mechanism in schematic detail.
Figure 8B:
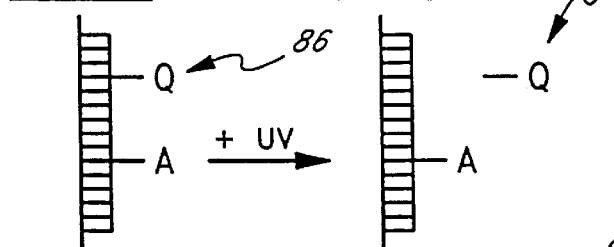
Figure 8C:
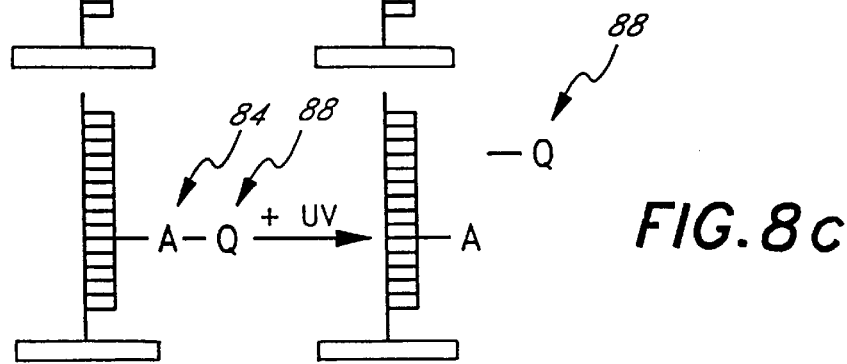

FIG. 8 shows various forms of write mechanism. Selective quenching is required to control the energy transfer process. Generally, three types of quenchers are preferred. The first group (FIG. 7a) involves UV sensitive quencher molecules 82 that are proximal to the fluorescent acceptor 84, and which prevent light emission. Upon exposure to UV radiation 86, the quencher 82 is inactivated (shown by an X in FIG. 7a) leaving the acceptor 84 free to reemit. The second mechanism (FIG. 7b) involves quencher molecules 86 which are organized proximal to the acceptor 84 by photocleavable linkers. Upon UV irradiation, the link is broken, allowing the quencher 86 to dissociate. The third mechanism (FIG. 7c) involves the derivitization of the acceptor 84 with photoactive groups 88. The quencher 88 makes the acceptor 84 nonfluorescent or "caged". Irradiation with UV light uncages the acceptor 84 and permits energy transfer and subsequent light emissions.

Figure 9:
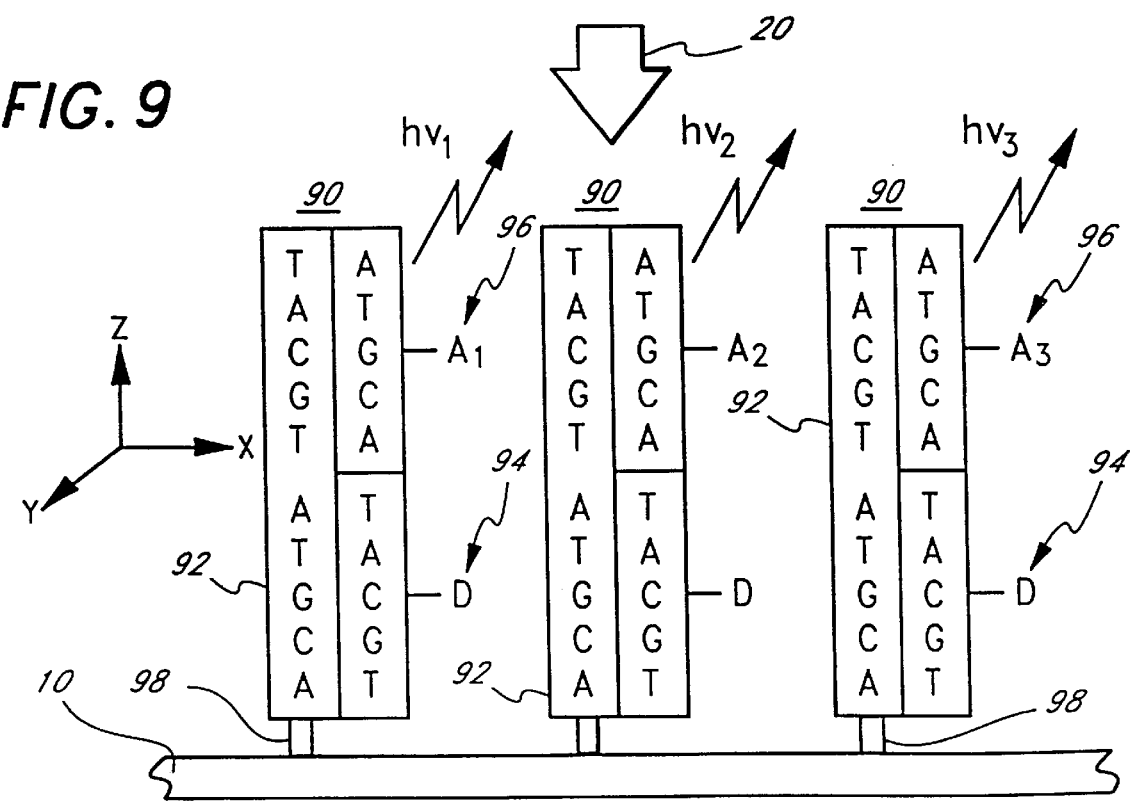
FIG. 9 shows the read mechanism in schematic detail.

FIG. 9 shows an end on view of three chromophoric memory units 90 attached to substrate 92. Each chromophoric memory unit 90 includes a template 92 to which the donors 94 and acceptors 96 may be attached. The chromophoric memory units 90 terminate in an attachment mechanism 98 which serves to anchor them to the substrate 10. Short illustrative sequences are shown for various donors 94 and acceptors 96 attached to complementary backbone sequences 92.

Figure 10A:
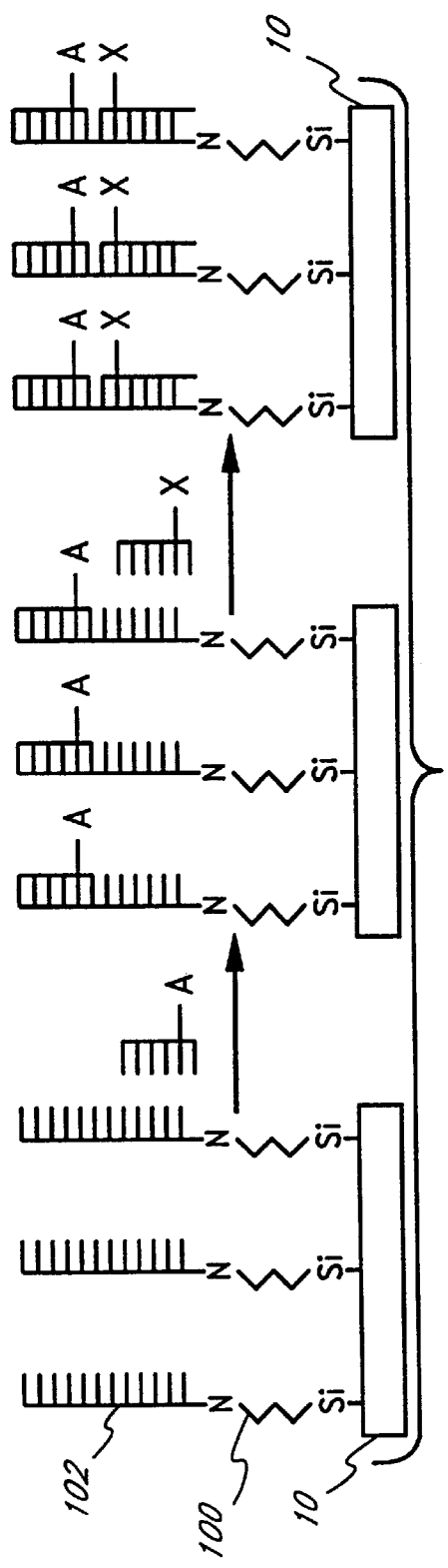
FIGS. 10a and 10b show the organization on unique and repetitive sequences.
Figure 10B:
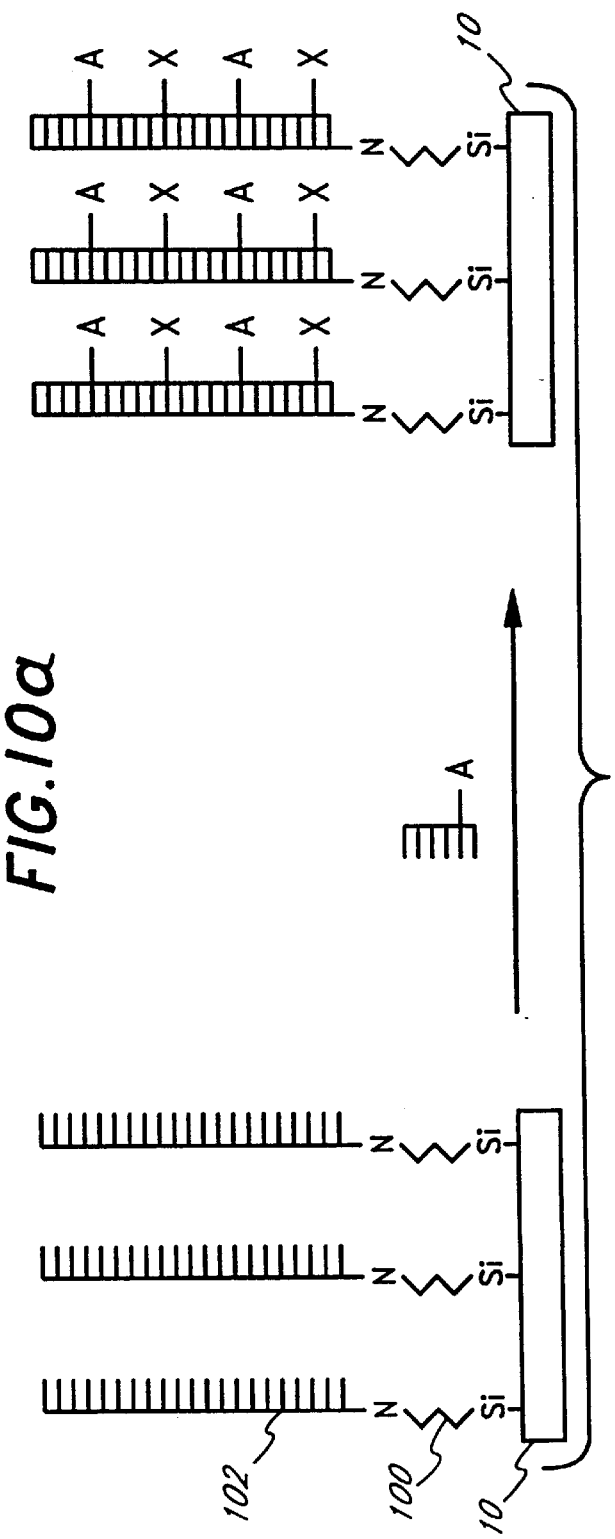

FIG. 10 shows the organization of DNA polymers on unique and repetitive attachment sequences. Substrates 10 have attachment mechanisms 100 to connect to backbones 102. The use of repetitive sequences allows more chromophoric units to be arranged in the z-dimension. The additional units increase or amplify the read signal. Additionally, if more "unique-repetitive" chromophoric units are added, then more information can be stored in the z-dimension. A synthetic DNA polymer containing 1000 nucleotides, could contain as many as 50 repetitive or unique-repetitive chromophoric unit sequences, and would extend approximately 340 nanometers (nm) in the z-dimension.

In one aspect of this invention, the read portal may be subdivided into various write subsections to increase the width of the data word read from the read portal. FIG. 11 shown a perspective view of a read portal 110 having 16 write subsections 112 located within the read portal 110. The write subsections 112 are defined to be those physical areas to which unique writing can occur. Utilizing current illumination techniques, an individual write sublocation 112 may be sized approximately (¼ micron)². For a 1 micron² read portal 110, 16 individual write subsections 112 can be included therein. While the write subsections 112 are shown as square in FIG. 11, they may be of any shaped desired, other preferable shapes including substantially circular or oval. Such a structure provides both spatial and spectrally resolvable aspects. If each write sublocation 112 contains acceptors which radiate at wavelengths which are spectrally resolvable from those wavelengths of the other write sublocations 112, the structure of FIG. 11 would result in the output of a 16-bit wide word for a single read illumination of the read portal 110. The various output wavelengths are shown in FIG. 11 as $\lambda_1$, $\lambda_2$, $\lambda_3$, $\lambda_4$, and continued on shown as $\lambda_8$, $\lambda_{12}$ and $\lambda_{16}$. In this embodiment, a single write wavelength may be utilized provide that it may be focused then to a single write sublocation 112. The dimensions for the preferred embodiment are shown on the figures.

FIG. 12 illustrates another aspect of this invention in which a read portal 120 contains multiple spatially resolved write sublocations 122 wherein within a given write sublocation 122 one or more detectable parameters are involved. Each write sublocation 122 preferably includes acceptors which have read wavelengths which are spectrally resolvable against all of the other read wavelengths from other write sublocations 122. The individual write sublocations 122 have labelled therein $\lambda_{1a}$, $\lambda_{1b}$, $\lambda_{1c}$, $\lambda_{1d}$, where the numerical subscript indicates the read detection wavelength and the alphabetical subscript indicates the state of the variation. One such variation is to vary the intensity for each color. The four states may be set at various intensity levels, for example, where $I_a=0\%$, $I_b=33\%$, $I_c=67\%$ and $I_d=100\%$. These percentages are not required, and may be set as desired to optimize detection accuracy and efficiency. A different variation within a given write sublocation 122 involves spectral shifts of each color. For example, the 'a' state could be no radiation from the write sublocation, the 'b' state the unmodified read wavelength, the 'c' state with the read wavelength increased by some amount, such as 5 nanometers and the 'd' state with a read detection wavelength decreased by some amount, such as 5 nanometers. The number of variation states available is equal to the number of write wavelengths available. With sufficient write wavelengths, a given read portal 120 could output 64 bits per square micron. Yet another variation involves the output polarization of the read wavelength.

Figures 13A, 13B:
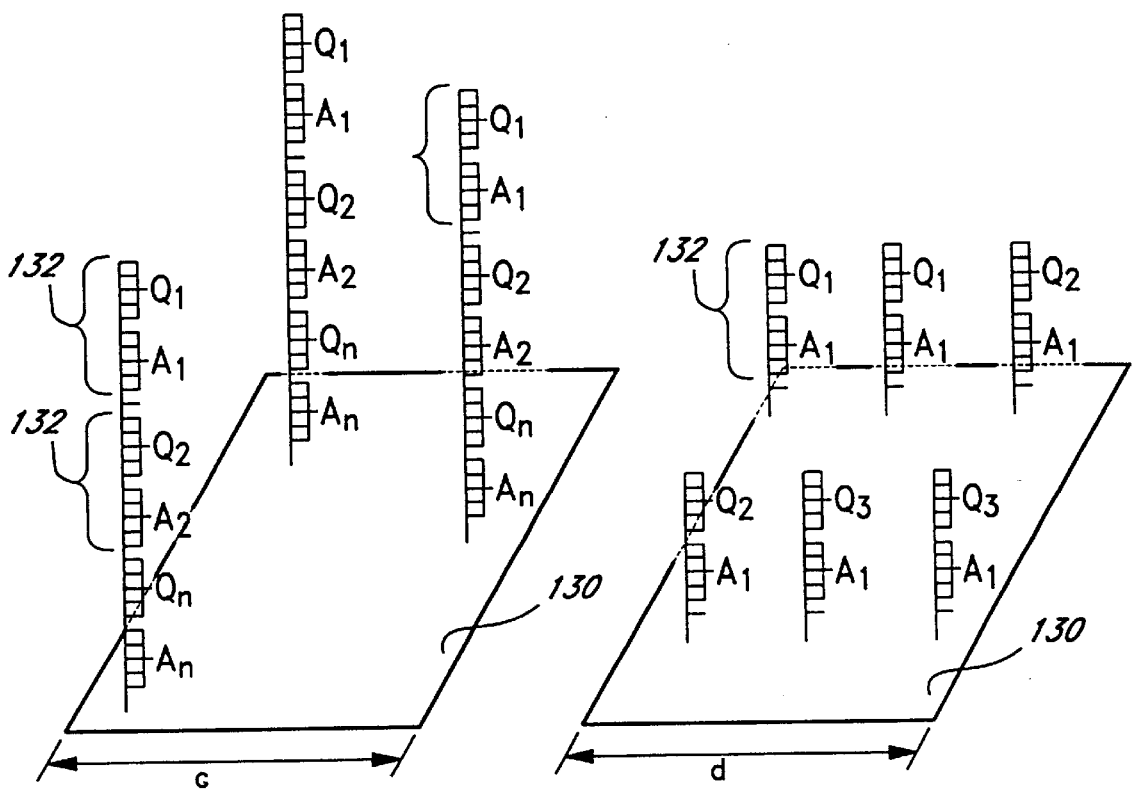
FIGS. 13a and 13b shows an organized DNA photonics structure.

FIG. 13 shows an organized DNA photonic structure for a complete read portal 130 and a write sublocation 132. In the read portal 130, paired quencher and acceptor units 132 are shown having n resolvable output characteristics, such as n spectrally resolvable wavelengths. The write sublocation 132 shows multiple pairs of quenchers and acceptors 132 in which the acceptors will all emit at a given wavelength, but the quenchers are subject to various resolvable write characteristics.

Figure 14:
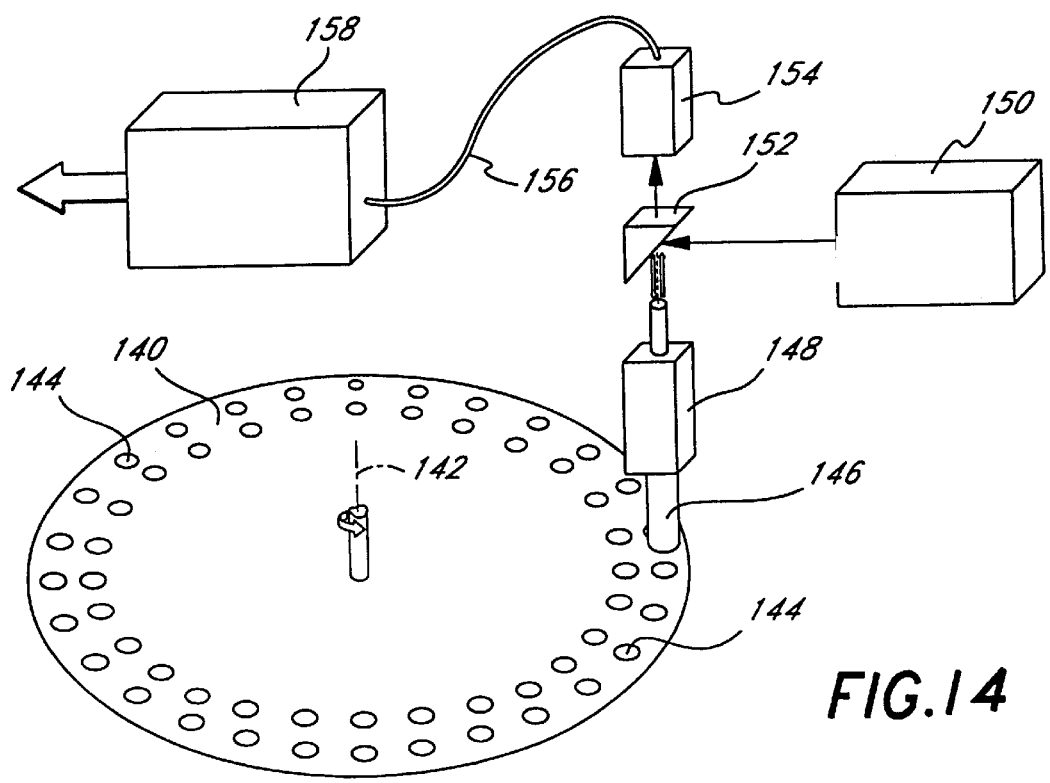
FIG. 14 shows a perspective view of the read detector system.

FIG. 14 shows a perspective view of an optical memory in accordance with the invention. A planar optical disk 140 is rotatable around an axis of rotation 142. A plurality of read portals 144 are disposed upon the surface of the optical disk 140. The optical portals 144 substantially cover the surface of the optical disk 140. In the preferred embodiments, the read portals 144 may be arranged in substantially circular tracks or in a spiral configuration as utilized for conventional optical disks or compact discs. The detector 146 is positioned proximally to the read portal 144 subject to reading. In the preferred embodiment, the detector 146 is a near field fiber optic. A positioning unit 148 serves to vary the spacing between the detector 146 and the surface of the optical disk 140. A source of read illumination 150, preferably a laser, is directed through optics to excite the chromophoric memory units within the read portal 144. In one embodiment, a dichroic mirror 152 may be utilized to direct the output of the laser through the detector 146. Emitted read illumination from the read portal 144 may be passed via the detector 146 through the optics, such as bandpass filters, including the dichroic mirror 132 to a read detector 154. In the preferred embodiment, the read detector 154 may be a single or array of avalanche photodiodes for parallel access. The detector 154 then provides a signal on cable 156 to output electronics 158. In an alternate embodiment, the optical disk may be illuminated from below the disk, with the detector remaining in the same position above the disk.

Figure 15:
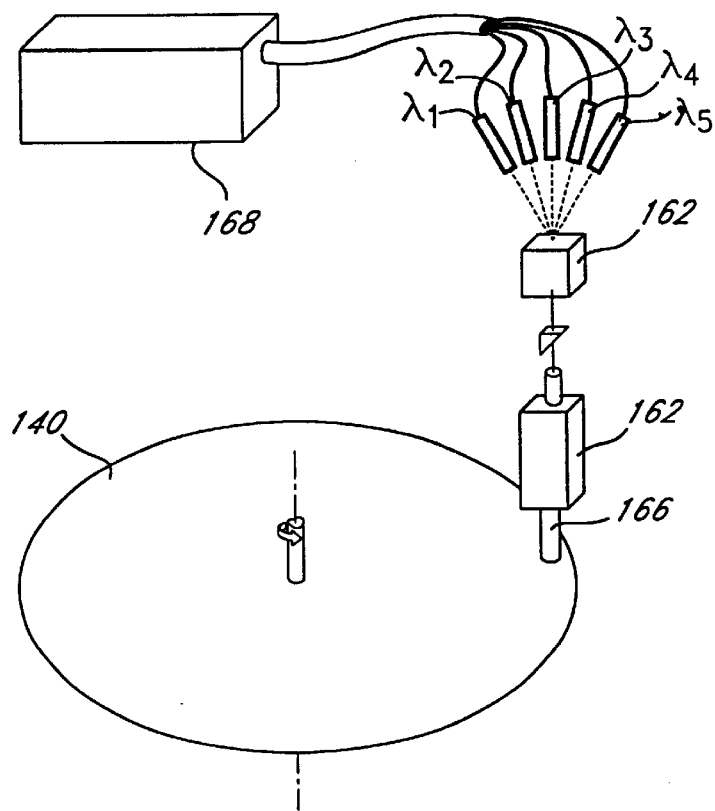
FIG. 15 shows a perspective view of the write device.

FIG. 15 shows a schematic view of the write device. The optical disk media 140 is adapted to rotate around its axis of rotation 142. The optical disk media 140 contains various chromophoric memory units in which the quencher is active in its initial state. During the course of the writing, the quencher may be inactivated. Multiple sources of illumination 160 are arranged to provide write illumination through alignment optics 162, preferably alignment optics, to a z positioner 164 and near field fiberoptic 166. In this way, any of the various sources of write illumination 160 may be directed to the chromphoric memory units disposed on the optical media 140. A write beam controller 168 is connected to the sources of illumination 160 to selectively activate the sources. As the optical disk media 140 rotates around its axis of rotation, the illumination from the sources 160 as controlled by the controller 168 illuminate various read portals or subportal size write locations. In this way, writing occurs as described previously (e.g., FIG. 5, FIG. 7b).

The detailed structure, sequence and chemistry of the memory will be described below. The discussion is generally divided to focus on DNA Design, Synthesis, Derivation, Attachment and Organization, Activation, Hybridization, Chromphoric Response and Write-Details.

Design

The sequences of nucleotides in the backbone 92 (FIG. 9) and complementary donor 94 and acceptor 96 sequences are designed preferably to self-organize by hybridization into discrete chromophoric units. The conventional nucleotide units of adenine (A), thymine (T), guanine (G) and cytosine (C) are arranged in various sequences. The conventional pairing is used, with adenine pairing with thymine and guanine pairing with cytosine. The conventional double helix structure is preferably utilized, wherein the standard radius is approximately 1.0 nm and spacing between base pairs is approximately 0.34 nm in a linear direction along the chain. Such DNA is desirable for use in the instant invention in part because of the precise geometric and distance requirements of Förster energy transfer photonics processes. Further, these sequences are designed for hybridization efficiency and specificity such that they can self-organize reproducibly into predicted arrangements of chromophore units. Additionally, the structures are preferably optimized for energy transfer efficiency. Finally, it is a desired aspect of the nucleotide sequences that they are attachable to the solid support, preferably the substrate 10.

These DNA sequences range from approximately 20 to 1000 nucleotides in length (i.e., base units adenine, cytosine, thymine, and guanine). The shorter DNA polymer sequences are generally referred to as Oligonucleotides or oligomers, and a DNA polymer 20 nucleotides in length would be designated a 20-mer. The actual molecular shape and size of a 20-mer would approximate a linear rod structure about 6.8 nanometers (nm) long and 1 nm in diameter (2 nm for double-stranded DNA). Each additional base unit would add 0.34 nm to the linear dimension. A 1000-mer would have a length of approximately 340 nm. Thus, we will be working with systems that are in the nanometer regime, reflecting a high degree of control and specificity. And, 20-mers to 1000-mers are easily synthesized with available automated instruments and other DNA technologies.

Sequences are preferably designed for the highest hybridization efficiency and specificity so that they will self-organize reproducibly into the planned molecular connections and arrangements. This precision is important because electronic transfer and photonic transfer (Förster) processes are highly dependent on maintaining control over distances between the photonic transfer groups or the charge transfer groups. Previous work in solution phase has shown DNA polymers can achieve this end. It is these mechanism and their associated geometric requirements that make synthetic DNA the optimal material for implementing a man-made system.

Consistent with the above stated design criteria for DNA structures useful with this invention, various useful and robust sets of building blocks have been formed for these photonic systems. The following DNA sequences have been designed for covalent attachment to metallized or silicon dioxide features on silicon surfaces.

Multiple DNA polymer attachment sequences have been synthesized with 3' terminal ribonucleosides. These were designed for covalent attachment to solid supports and the organization of chromophore labelled polymer sequences. Twelve (12) amine or aldehyde functionalized sequences were synthesized for reaction with chromophore groups. From those 12 DNA sequences, 26 DNA-chromophore derivatives were made consisting of 8 distinct colors, 1 quencher and 1 UV sensitive caged chromophore. Table 1 shows the current DNA-chromophore conjugates currently available.

TABLE 1

DNA-Chromophore Conjugates

| Chromophore | Ex/Em(nm) | DNA-Chromophore Conjugate |
|---|---|---|
| Fluorescein: | 494/519 | DO-1F, DO-2F, DO-3F, DOA, DOB, DOC, DOD, DOE, ET-10-F, ET-11-F, T2-F |
| Rhodamine T: | 544/570 | T2-RT |
| Rhodamine X: | 570/596 | T2-RX |
| Bodipy 1: | 558/568 | ET-14 |
| Bodipy 2: | 530/550 | T2 |
| Lucifer Yellow: | 428/533 | ET-10-LY, ET-11-LY |
| Texas Red: | 589/615 | ET-10-TR, ET-11-TR, ET-12R-TR, ET-14-TR, ET-21A-TR, T2-TR |
| Napthofluorescein: | 600/672 | T2-NF |
| Caged Carboxy-fluorescein | 494/519* | ET-13-CF |
| Malachite Green: | 627/none | ET-11-MG |

*Fluorescent when uncaged by exposure to UV light < 365 nm.

Figure 16:
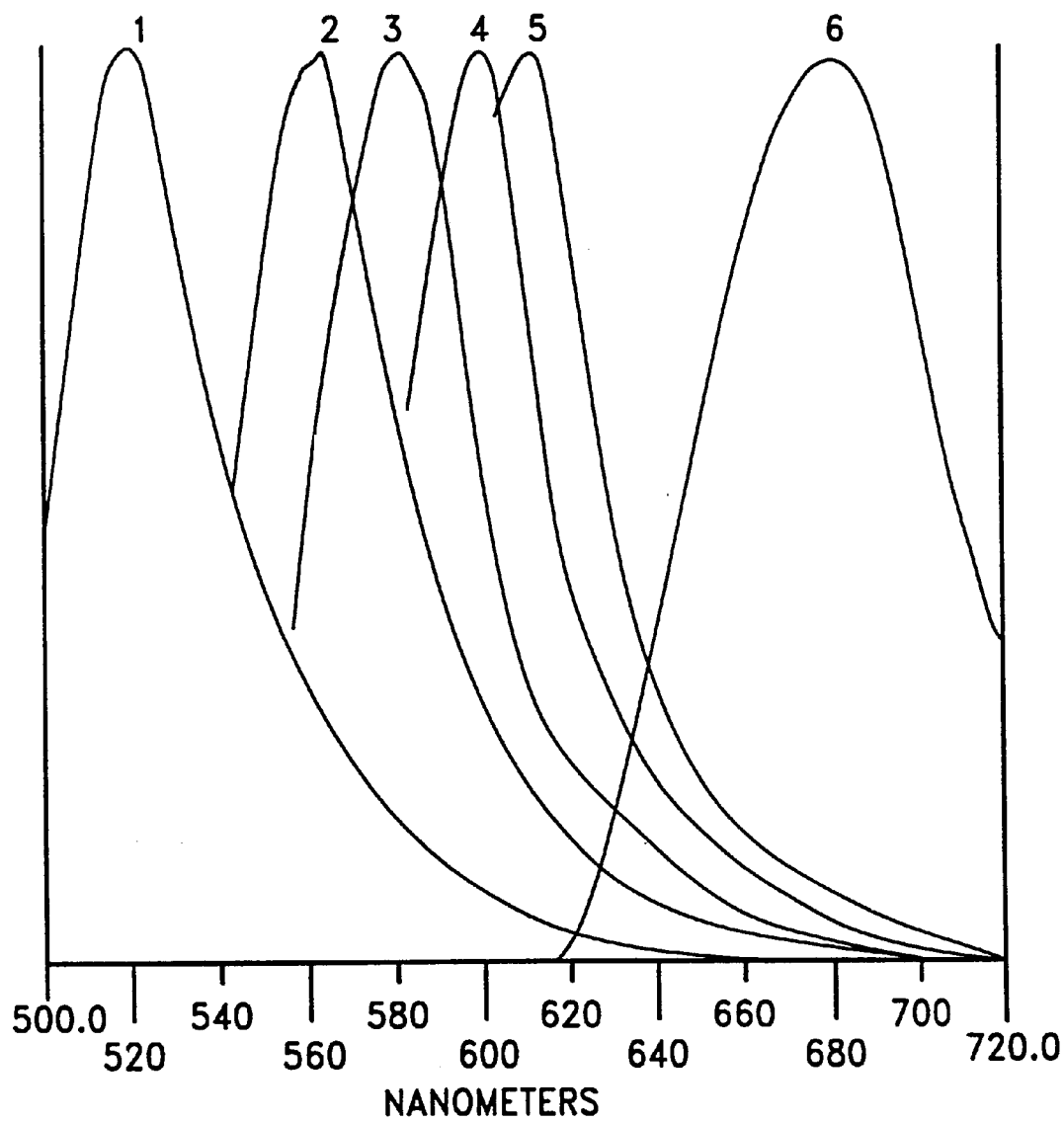
FIG. 16 shows multi-wavelength spectra for various acceptor units.

FIG. 16 shows a graph of the intensity as a function of wavelength for the six polymer sequences.

The spectra for the six curves are listed below in Table 2.

| Peak | DNA-Chromophore | Excitation (nm) | Emission (nm) |
|---|---|---|---|
| 1 | T2-Fluorescein | 494 | 519 |
| 2 | T2-Bodipy 2 | 530 | 550 |
| 3 | T2-Rhodamine T | 544 | 570 |
| 4 | T2-Rhodamine X | 570 | 596 |
| 5 | T2-Texas Red | 589 | 615 |
| 6 | T2-CN Fluorescein | 600 | 672 |

Figure 17A:
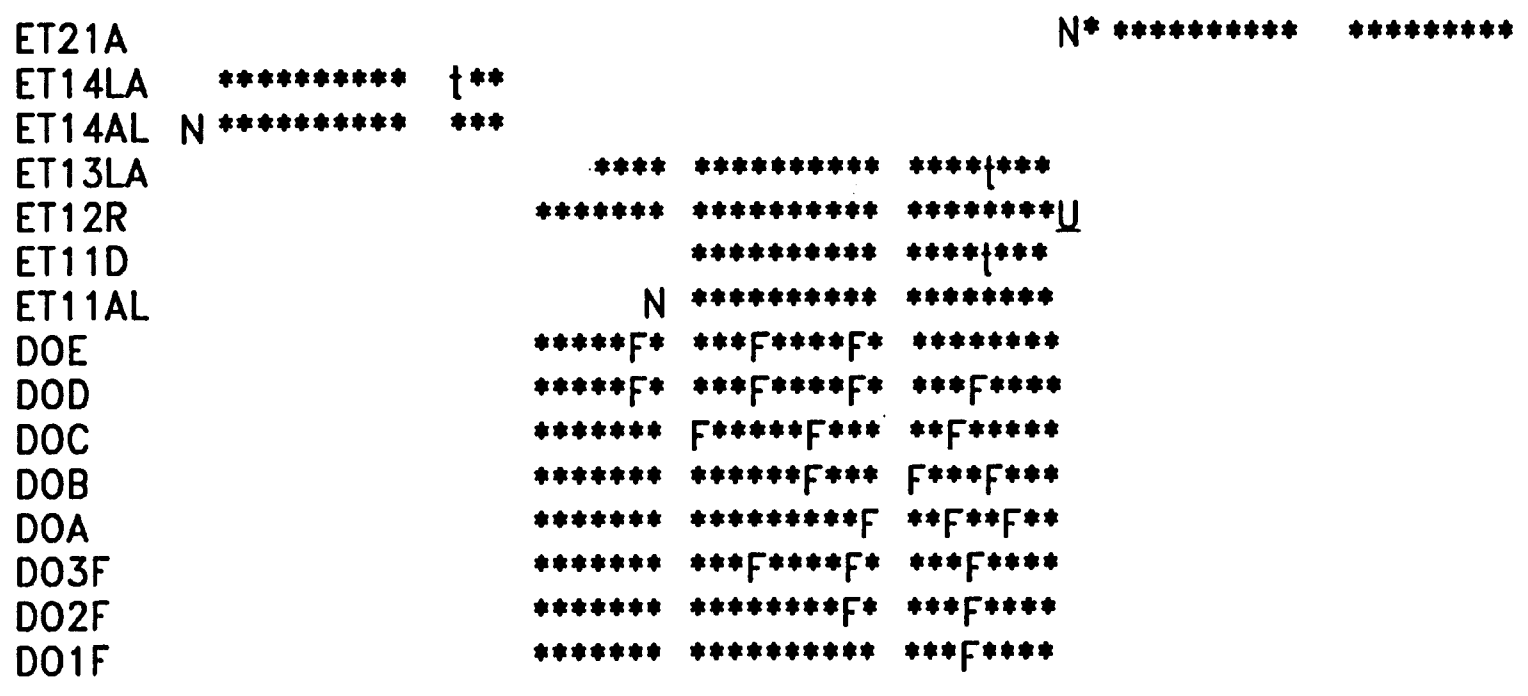

FIG. 17 shows an enhanced DNA polymer map. this map indicates the sequences of all the various DNA chromophore units relative to the attachment sequences. The * positions indicate the nucleotide sequence which is similar to the sequences at the center of the diagram.

In addition to the sequences presented in FIG. 14, additional sequences have been designed which allow repetitive chromophoric DNA units to be constructed. These include the attachment sequences ATT-1-6; the template sequences TEM-1-6; and the chromophoric sequences PET-1-C. The attachment sequences (ATT) are listed below (5' and 3' refer to directionality of the DNA sequence):

ATT-1 5'-GGCTAGCCGATCGGGTCCTCAGGTCAAG TCAAT-rA-3' (SEQUENCE ID NO.1)

ATT-2 5'-CGCACTATGGTCGTGAGTGTTCAGAGGC TATCAG-3' (SEQUENCE ID NO.2)

ATT-3
5'-GAGAGACTCATGAGCAGGGGCTAGCCGA TCGGG-rA-3' (SEQUENCE ID NO.3)

ATT-4
5'-GACTTGACCTGAGGACCCGATCGGCTAGC CCCTGCT-3' (SEQUENCE ID NO. 4)

ATT-5
5'-ATGTCTGACTGCAGCTCGCACGAGAGACT ATGAGC-rA-3' (SEQUENCE ID NO.5)

ATT-6
5'-GCTAGCCCCTGCTCATGAGTCTCTCGTGC GGCTGC-3' (SEQUENCE ID NO.6)

The following specific DNA sequences have been designed to form templates, or to be useful as repeating structures for spanning distances greater than substantially 100 nanometers. The template sequences (TEM) are listed below:

TEM-1
5'-ATTGACTTGACCTGAGGACCCGATCGGCTA GCCCCAAGCTTGCATGCCTGCAGGTCGACTC TAGAGGATCCCCGGGTACCGAGCTCGAATTC-3' (SEQUENCE ID NO.7)

TEM-2 5'-GAATTCGAGCTCGGT-GAATTCGAGCTCGGTACCCGGGGATCCTCTA GAGTCGACCTGCAGGCATGCAAGCTTGGCCC AAGCTTGGCTGCAGGT-3' (SEQUENCE ID NO.8)

TEM-3 5'-ACCTGCAGCCAAGCTTGG-CATGATTACGAATTCCCGGGGATCCGTCGACC TGCAGCCAAGCTTGGCACTAGCCTCTGAACA CTCACGACCATA-3' (SEQUENCE ID NO.9)

TEM-4
5'-TATGCTTCCGGCTCGTATGTTGTGTGGAATT GTGAGCGGATA-3' (SEQUENCE ID NO.10)

TEM-5
5'-GTCATAGCTGTTTCCTGTGTGAAATTGTTAT CCGCTCACAAT-3' (SEQUENCE ID NO.11)

TEM-6
5'-ACGTTGTAAAACGACGGCCAGTGCCAAGCT TGGCTGCAGAG-3' (SEQUENCE ID NO.12)

Specific DNA sequences have been designed for functionalization with various photonic transfer (chromophore or fluorophore) groups and electronic transfer (charge transfer) groups. The photonic/electronic transfer sequences (PET) are listed below:

PET-1 5'-CCGGGGATCCTCTAGAGTCGA-3' (SEQUENCE ID NO. 13)

PET-2 5'-CCTGCAGGCATGCAAGCTTGG-3' (SEQUENCE ID NO. 14)

PET-3
5'-GCCAAGCTTGCATGCCTGCAGGTCGACTCT-3' (SEQUENCE ID NO.15)

PET-4
5'-AGAGGATCCCCGGGTACCGAGCTCGAATTC-3' (SEQUENCE ID NO.16)

PET-5 5'-AGTGCCAAGCTTGGCTGCAGGTCG-3' (SEQUENCE ID NO.17)

PET-6 5'-ACGGATCCCCGGGAATTCGTAATCATG-3' (SEQUENCE ID NO.18)

Syntheses

The synthesis of short DNA polymer sequences of from approximately 10 to approximately 100 monomers is a straight forward task for those of ordinary skill in the art. Automated DNA polymer synthesizers, such as those from Applied Biosystems (Foster City, Calif.) automatically synthesize using conventional phosphoramidite chemistry. In operation, the nucleoside at the 3'-terminus is attached to a controlled pore glass support by means of a linker arm. The 5'-terminus is blocked with a dimethoxytrityl (DMT) group. First, the support bound nucleoside is deprotected to provide a free 5'-hydroxyl group for the attachment of the next nucleotide. The second nucleotide is deblocked and activated at the 3'-hydroxyl with tetrazole to form a highly reactive intermediate. The 5'-terminus is blocked with DMT to prevent self polymerization. Next, a capping step renders any chains which do not undergo addition inert to further additions. The internucleotide linkage is then oxidized from the phosphite to the more stable phosphate. After oxidation, the DMT is removed from the growing DNA chain and the cycle is repeated until chain elongation is complete. Finally, the fully assembled oligonucleotide is cleaved from the CPG support, deprotected and purified by polyacrylamide gel electrophoresis (PAGE) or high pressure liquid chromatography (HPLC) to remove failure sequences.

The attachment sequences contain 3'-terminal ribonucleoside and are synthesized by initiating synthesis from a ribonucleoside-CPG support. Certain homopolymer attachment sequences are synthesized by enzymatic reaction, and may be purchased from commerical sources such as Sigma Chemicals (St. Louis, Mo.). Other sequences may contain amine functionalities and serve as substrates for the attachment of chromophore molecules, including the donor, acceptor and/or quencher molecules. These polymers have a 5'-terminal amine and internal primary amine groups. The 5'-terminal amine functionalities are automatically incorporated by means of the ABI amino link to reagent. Internal labelling of the oligonucleotide is done by several methods. In the case of fluorescein the chromophore is automatically incorporated into the polymer at any position through use of a fluorescein phosphormidite. For labelling with other chromophores, an amine terminated linker arm nucleoside phosphormidite is automatically incorporated into the polymer at any thymine base position.

Derivitization

Derivitization is performed in the preferred embodiment as follows:

The amine functionalized synthetic DNA polymers are labelled with chromophore groups and are used in the energy transfer, quenching and a write mechanism. Many chromophore groups are commerically available in reactive forms which allow straight forward coupling chemistry to amine groups. The different chromophores are generally available in at least one of the reactive forms listed below:

1. Isothiocyanates (R—N=C=S) which form thioureas (R=NH—[C=S]—NH—R') upon reaction with amines. Fluorescein, tetramethylrhodamine and rhodamine X DNA conjugates are formed by this chemistry.
2. Succinimidyl esters (R—CO$_2$—X) which form carboxamidesg R—[C=O]—NH—R') upon reaction with amines. Bodipy dyes, napthofluorescein and caged carboxyfluorescein conjugates are formed by this chemistry.
3. Sulfonyl chlorides (R—SO$_2$Cl) which form stable sulfonamides (R—[SO2]—NH—R') upon reaction with amines. Texas Red conjugates are formed by this chemistry.

The typical labeling conditions are as follows:

1. Dissolve the amine containing oligo in 0.25 M sodium bicarbonate, pH 9.0–9.1 to a final concentration of 1 O.D./units (~5 mM for a 20 mer). Substitute sodium bicarbonate, pH 8.3 (uncorrected for reactions with succinimidyl esters.
2. Dissolve the amine reactive chromophore derivative in anhydrous dimethylformamide (DMF) to a final concentration of ~100 mM.
3. Combine 10 ul of DNA and 20 ul chromophore, chromophore/DNA and incubate at room temperature for 1–2 hours.
4. Add 5 ul concentrated ammonia to quench unreacted material.
5. Purify the material by passing through a G-25 Sephadex column (0.9×10 cm) equilibrated in 5 mM sodium acetate, pH 7.0

6. Collect fractions and measure absorbance on spectrophometer from 230–650 nm. DNA absorbs at ~260 nm and the chromophore absorbs at its excitation maximum.
7. Pool conjugate fractions. Reaction usually go to >50% completion.
8. Analyze 0.1 O.D. product by 20% polyacrylamide gel electrophoresis.
9. Lyophilize sample to dryness and re-suspend at 1 O.D./ul in 5 mM sodium acetate.
10. Load sample onto a preparative 20% PAGE and let xylene cyanol tracking dye run ~10 cm into the gel.
11. By UV backshadowing, cut out gel slice containing both UV absorbing and fluorescent material.
12. Crush the gel slice containing product with a mortar and pestle and elute product overnight in 1×SSC buffer (0.15 M sodium chloride, 0.015 M sodium citrate, pH 7.0).
13. Load the elute onto a pre-equilibrated $C_{18}$ Sep Pak (Millipore, Milford, Mass.) reverse phase column to remove contaminating polyacrylamide.
14. Wash the column with 20 mls water.
15. Elute the product with 2 mls of 50% acetonitrile.
16. Analyze the elute spectrophometrically and then lyophilize to dryness.
17. Resuspend final product to 1 O.D./ul in 5 mM sodium acetate, pH 7.0. Typical yields of pure final product are approximately 50% of the starting amount.

Attachment—Organization

Figure 18:
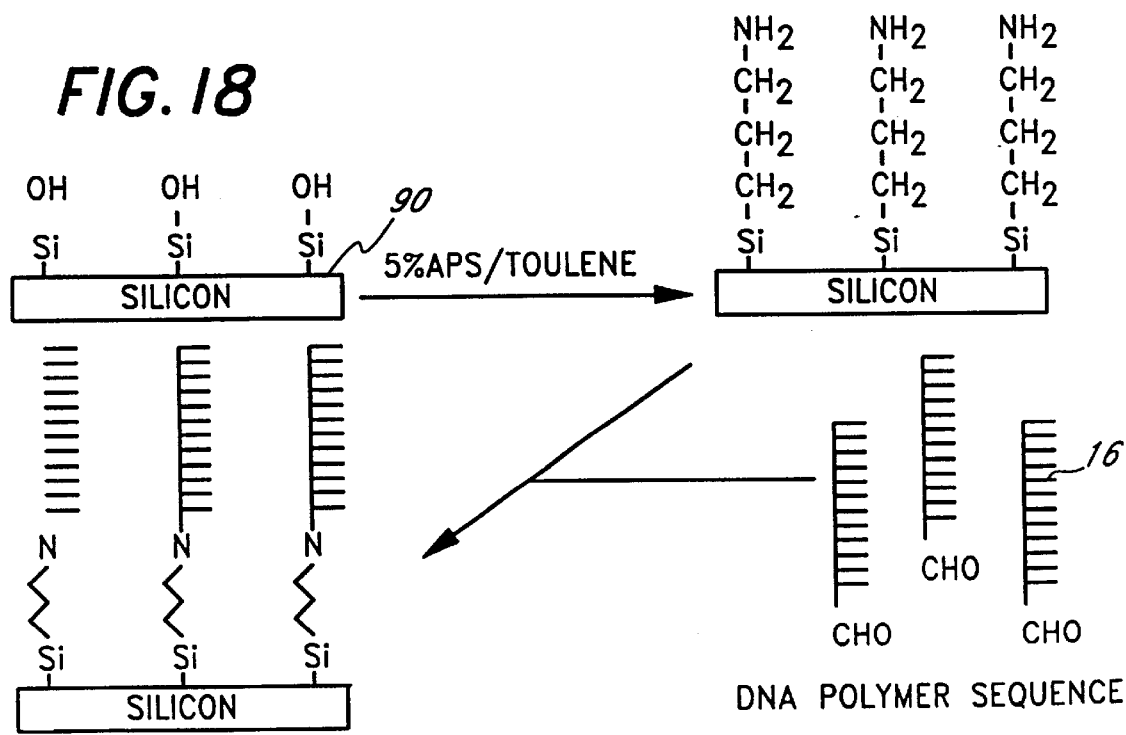
FIG. 18 shows the DNA attachment chemistry cycle.

FIG. 18 shows the steps associated with the preferred attachment chemistry for affixing the chromophoric memory units 16 to the substrate 10. (See FIG. 1). The surface of the substrate 90 is amine functionalized with APS. These then react with aldehyde terminated DNA to form a covalent bond.

The chromophoric memory units are attached to the substrate, either directly or through an intermediary. In the preferred process, a two step process is utilized. First, the solid surface is activated with primary amine groups. Second, the DNA attachment sequence is converted to an intermediate form which reacts with amine groups. The attachment chemistry is stable and robust and is successful on a variety of substrates, including glass, silicon and metal oxides. The support bound DNA retains all of its hybridization properties relative to hybridization efficiency and non-specific background. A surface loading factor of approximately $10^5$–$10^6$ DNA attachment sequences per micron$^2$ is obtained.

Substrate surfaces are amine functionalized by 3-aminopropyltriethoxysilane (APS, Aldrich Chemical Co., Milwaukee, Wis.) which reacts readily with the oxide and/or hydroxyl groups on metal and silicon surfaces and provides a primary amine functionality. Next, the attachment sequence is converted to a reactive dialdehyde form by the periodate oxidation methods. The amine and aldehyde groups react readily to form a stable imine or Schiff's base. The APS reaction is performed by treating the desired surface for 30 minutes with a 10% (v/v) solution of APS in toulene at 50° C. The surface is then washed 3 times in toulene, 3 times in alcohol and then air dried for 60 minutes at 50° C. The resultant surface is amine functionalized and is extremely reactive to aldehyde groups present on the periodate oxidized attachment sequences.

Activation

DNA activation is accomplished in the preferred embodiment by the following process. The 3'-terminal ribonucleotide terminus of the attachment sequences is converted to a terminal dialdehyde by the periodate oxidized method. The periodate oxidation reaction is performed as 1 O.D/ul. 1 volume of 0.1 M sodium acetate, pH 5.2 and 1 volume of 0.45 M sodium periodate (made fresh in water) is added. The reaction is stirred and incubated at room temperature for at least 2 hours protected from light. The reaction mix is then loaded onto a Sephadex G-10 column (pasteur pipette, 0.6×5.5 cm) which is equilibrated in 0.1 M sodium phosphate, pH 7.4. Fractions (200 ul) are collected and 2 ul aliquots are spoted onto silica TLC plates. The UV absorbing fractions are combined and contain the activated DNA polymer.

The solid support materials is rinsed with 0.1 M sodium phosphate, pH 7.4. Aspirate and add buffer sufficient to cover the chips, add the periodate oxidized attachment sequences, at minimum 1 O.D. per $cm^2$ of surface area. Mix well and react 1–2 hours at room temperature. The carbonyl compounds form covalent adducts with amines by dehydration to imines or Schiff's bases. The DNA substrate are then washed twice with sodium phosphate buffer, twice with 1×SSC, 0.1% SDS (WB=0.15 M sodium chloride, 0.015 M sodium citrate, pH 7.0 and 0.1% (w/v) sodium dodecyl sulfate) and twice with 1×SSC (0.15 M sodium chloride, 0.015 M sodium citrate, pH 7.0). The derivatized materials are used immediately or stored dry.

Hybridization

The preferred hybridization process is accomplished utilizing any techniques satisfactory to meet the functional criteria of the invention. In the preferred embodiment, the following hybridization technique is used. The DNA support substrates are hybridized for 5 minutes with 100–200 nM complementary polymer sequences containing a fluorescent group at 37–50° C. in 5×SSC, 0.1% SDS (HB). The hybridization temperature is estimated by the DNA sequence composition and by using the formula, $T_m \times (2 \times A/T) + (4 \times G/C)$. For example, the hybridization temperature for ET-10AL would be $(2 \times 8) + (4 \times 10) = 56°$ C. The actual hybridization temperature is 10° C. lower (45° C.) to maximize the extent of hybridization. The support substrates are washed 3 times in prewarmned WB at temperature, 1 minute each. Finally the support substrates are rinsed in 1×SSC at RT and dried by canned air (i.e., Dust-Off). The support substrates are mounted on a glass slide and observed by epifluorescence with a Jenna Epifluorescent microscope fitted with a Hamamatsu intensified CCD (ICCD) camera imaging system.

A loading factor of approximately $10^5$–$10^6$ attachment sequences/$um^2$ is generally adequate. The loading factor is variable because the APS chemistry modifies the oxides or hydroxyl groups whose concentration is dependent upon processing factors.

Chromophoric Response

Chromophoric groups which emit fluorescence in the generally 500–800 nanometer range and are reactive with DNA and the amine labelling chemistry are listed below:

| Fluorescent Donor/Acceptor Derivatives: | |
|---|---|
| Texas Red | (Em = 610 nm) |
| Rhodamine | (Em = 580 nm) |
| Bodipy Dyes | (Em = 503, 514, 550, 568, 570, 588, 594 nm) |
| Lucifer Yellow | (Em = 528 nm) |
| Fluorescein | (Em = 520 nm) |
| Cascade Blue | (Em = 425 nm) |
| Non-Fluorescent Donor/Quencher Derivatives: | |
| Dimethylaminophenylazophenyl (DABITC) | |
| Reactive Red | |
| Malachite Green | |

The various wavelengths output from a read portal must be spectrally resolvable. Utilizing current detection techniques, peak separations of from approximately 10 to 20 nanometers between each color are resolvable.

Various photoactive groups with selective UV absorption characteristics useful for the write mechanism include:

| | |
|---|---|
| p-Methoxybenzyl Ethers | ~280 nm |
| p-Nitrobenzyl Ethers | ~280 nm |
| p-methoxyphenacyl Esters | ~300 nm |
| o-Nitrobenzyl Ethers | ~320 nm |
| Pyrenymethyl Esters | ~340 nm |
| bis-2-Nitrobenzyl Acetals | ~350 nm |

Write Details

The caging group approach has been prepared as follows. A cage fluorescein (fluorescein-bis-dimethoxynitrobenzyl ether) is commerically available as a succinimidyl ester derivative. An ET-13-caged fluorescein (ET-13-CF) conjugate is made. The compound is intrinsically nonfluorescent until exposed to UV radiation at less than 365 nanometers. Upon irradiation, the compound becomes intensely fluorescent at the characteristic fluorscene excitation and emission maxima, 490 and 520 nanometers, respectively. See FIG. 15.

Although the invention has been described with respect to specific preferred embodiments, many variations and modifications may become apparent to those skilled in the art. It is therefore the intention that the appended claims be interpreted as broadly as possible in view of the prior art to include all such variations and modifications.

We claim:

1. An optical memory comprising:
   a plurality of read portals disposed on a substrate, and
   chromophoric memory units disposed within the read portals, each chromophoric memory unit adapted to receive photonic energy, to transfer energy in a non-radiative manner, and to re-emit energy based upon the action or non-action of a quencher.

2. The optical memory of claim 1 where the substrate is a round platter.

3. The optical memory of claim 2 where the portals are disposed upon the platter in radial tracks.

4. The optical memory of claim 2 where the portals are located on a radial spiral.

5. The optical memory of claim 1 wherein the read portals include multiple write sublocations.

6. The optical memory of claim 5 wherein each of the multiple write sublocations has resolvable read parameters.

7. The optical memory of claim 6 wherein the resolvable read parameter is wavelength.

8. The optical memory of claim 6 wherein the resolvable read parameter is intensity.

9. The optical memory of claim 6 wherein the resolvable read parameter is polarization.

10. The optical memory of claim 1 wherein the substrate has a substantially planar surface upon which the read portals are disposed.

11. The optical memory of claim 10 wherein the read portals are planar to the substrate surface.

12. The optical memory of claim 10 wherein the read portals are located below the substrate surface.

13. The optical memory of claim 10 wherein the read portals are disposed in wells below the substrate surface.

14. The optical memory of claim 10 wherein the read portals are raised above the substrate surface.

15. The optical memory of claim 10 wherein the read portal is substantially circular.

16. The optical memory of claim 10 wherein the read portal is substantially square.

17. The optical memory of claim 1 where the chromophoric memory unit includes:
   a DNA template,
   a donor group,
   an acceptor group, and
   a quencher group.

18. A memory cell in an optical memory comprising:
   a support substrate,
   an attachment mechanism attached to the substrate, and
   a chromophoric memory unit, coupled to the attachment mechanism, the chromophoric memory unit comprising,
   a DNA template, and
   functionalized DNA including a donor group, an acceptor group and a quencher group, the donor group and acceptor group being positioned for non-radiative energy transfer.

19. The memory cell of claim 18 wherein the support is a substrate.

20. The memory cell of claim 19 wherein the substrate is chosen from the following group: silicon, silicon dioxide and metal.

* * * * *

SEQUENCE LISTING

<160> NUMBER OF SEQ ID NOS: 18

<210> SEQ ID NO 1
<211> LENGTH: 33
<212> TYPE: DNA
<213> ORGANISM: synthetic construct

<400> SEQUENCE: 1

-continued ggctagccga tcgggtcctc aggtcaagtc aat                          33

<210> SEQ ID NO 2
<211> LENGTH: 34
<212> TYPE: DNA
<213> ORGANISM: synthetic construct

<400> SEQUENCE: 2
cgcactatgg tcgtgagtgt tcagaggcta tcag                         34

<210> SEQ ID NO 3
<211> LENGTH: 33
<212> TYPE: DNA
<213> ORGANISM: synthetic construct

<400> SEQUENCE: 3
gagagactca tgagcagggg ctagccgatc ggg                          33

<210> SEQ ID NO 4
<211> LENGTH: 36
<212> TYPE: DNA
<213> ORGANISM: synthetic construct

<400> SEQUENCE: 4
gacttgacct gaggacccga tcggctagcc cctgct                       36

<210> SEQ ID NO 5
<211> LENGTH: 36
<212> TYPE: DNA
<213> ORGANISM: synthetic construct

<400> SEQUENCE: 5
atgtctgact gcagctcgca cgagagactc atgagc                       36

<210> SEQ ID NO 6
<211> LENGTH: 36
<212> TYPE: DNA
<213> ORGANISM: synthetic construct

<400> SEQUENCE: 6
gctagcccct gctcatgagt ctctcgtgcg agctgc                       36

<210> SEQ ID NO 7
<211> LENGTH: 92
<212> TYPE: DNA
<213> ORGANISM: synthetic construct

<400> SEQUENCE: 7
attgacttga cctgaggacc cgatcggcta gccccaagct tgcatgcctg caggtcgact    60
ctagaggatc cccgggtacc gagctcgaat tc                                 92

<210> SEQ ID NO 8
<211> LENGTH: 93
<212> TYPE: DNA
<213> ORGANISM: synthetic construct

<400> SEQUENCE: 8
gaattcgagc tcggtgaatt cgagctcggt acccggggat cctctagagt cgacctgcag    60
gcatgcaagc ttggcccaag cttggctgca ggt                                93

<210> SEQ ID NO 9
<211> LENGTH: 93

```
<212> TYPE: DNA
<213> ORGANISM: synthetic construct

<400> SEQUENCE: 9
acctgcagcc aagcttggca tgattacgaa ttcccgggga tccgtcgacc tgcagccaag      60
cttggcacta gcctctgaac actcacgacc ata                                   93

<210> SEQ ID NO 10
<211> LENGTH: 42
<212> TYPE: DNA
<213> ORGANISM: synthetic construct

<400> SEQUENCE: 10
tatgcttccg gctcgtatgt tgtgtggaat tgtgagcgga ta                         42

<210> SEQ ID NO 11
<211> LENGTH: 42
<212> TYPE: DNA
<213> ORGANISM: synthetic construct

<400> SEQUENCE: 11
gtcatagctg tttcctgtgt gaaattgtta ccgctcaca at                          42

<210> SEQ ID NO 12
<211> LENGTH: 41
<212> TYPE: DNA
<213> ORGANISM: synthetic construct

<400> SEQUENCE: 12
acgttgtaaa acgacggcca gtgccaagct tggctgcaga g                          41

<210> SEQ ID NO 13
<211> LENGTH: 21
<212> TYPE: DNA
<213> ORGANISM: synthetic construct

<400> SEQUENCE: 13
ccggggatcc tctagagtcg a                                                21

<210> SEQ ID NO 14
<211> LENGTH: 21
<212> TYPE: DNA
<213> ORGANISM: synthetic construct

<400> SEQUENCE: 14
cctgcaggca tgcaagcttg g                                                21

<210> SEQ ID NO 15
<211> LENGTH: 30
<212> TYPE: DNA
<213> ORGANISM: synthetic construct

<400> SEQUENCE: 15
gccaagcttg catgcctgca ggtcgactct                                       30

<210> SEQ ID NO 16
<211> LENGTH: 30
<212> TYPE: DNA
<213> ORGANISM: synthetic construct

<400> SEQUENCE: 16
agaggatccc cgggtaccga gctcgaattc                                       30
```

```
<210> SEQ ID NO 17
<211> LENGTH: 24
<212> TYPE: DNA
<213> ORGANISM: synthetic construct

<400> SEQUENCE: 17
agtgccaagc ttggctgcag gtcg                                              24

<210> SEQ ID NO 18
<211> LENGTH: 27
<212> TYPE: DNA
<213> ORGANISM: synthetic construct

<400> SEQUENCE: 18
acggatcccc gggaattcgt aatcatg                                           27
```